United States Patent
Harlin et al.

(10) Patent No.: US 8,329,970 B2
(45) Date of Patent: Dec. 11, 2012

(54) DEOXYGENATION OF MATERIALS OF BIOLOGICAL ORIGIN

(75) Inventors: Elina Harlin, Kerava (FI); Helka Turunen, Porvoo (FI); Johan-Fredrik Selin, Helsinki (FI); Marja Tiitta, Porvoo (FI); Mohamed Lashdaf, Porvoo (FI)

(73) Assignee: Neste Oil Oyj, Espoo (FI)

( * ) Notice: Subject to any disclaimer, the term of this patent is extended or adjusted under 35 U.S.C. 154(b) by 623 days.

(21) Appl. No.: 12/579,224

(22) Filed: Oct. 14, 2009

(65) Prior Publication Data
US 2011/0087058 A1    Apr. 14, 2011

Related U.S. Application Data

(60) Provisional application No. 61/105,953, filed on Oct. 16, 2008.

(51) Int. Cl.
*C07C 1/00* (2006.01)
*C10L 5/00* (2006.01)

(52) U.S. Cl. ......... 585/240; 585/242; 585/700; 44/605; 44/606

(58) Field of Classification Search ........... 585/240, 585/242, 700; 44/605, 606
See application file for complete search history.

(56) References Cited

U.S. PATENT DOCUMENTS

| | | | |
|---|---|---|---|
| 4,038,172 A | * | 7/1977 | Ueda et al. ............ 585/242 |
| 4,266,083 A | * | 5/1981 | Huang .................. 585/240 |
| 5,200,063 A | * | 4/1993 | Neskora et al. .......... 208/400 |
| 5,705,722 A |   | 1/1998 | Monnier et al. |
| 2007/0131579 A1 |   | 6/2007 | Koivusalmi et al. |

FOREIGN PATENT DOCUMENTS

| | | |
|---|---|---|
| EP | 1396531 B1 | 3/2007 |
| FI | 100248 B | 8/1997 |
| GB | 335543 | 9/1930 |

OTHER PUBLICATIONS

Maier, W.F. et al., "Gas Phase Decarboxylation of Carboxylic Acids", Chemische Berichte, 1982, vol. 115 (2), pp. 808-812.
Parmon, "Catalytic technologies for energy production and recovery in the future", Catalysis Today, vol. 35, 1997, pp. 153-162, XP002519024, p. 155.
Thomson, W.J. et al., "Homogeneous Catalytic Reduction of Benzaldehyde with Carbon Monoxide and Water, Applications of the Water Gas Shift Reaction" ACS Symposium Series, 1981, vol. 152 (Catal. Act. Carbon Monoxide), pp. 133-145.

* cited by examiner

*Primary Examiner* — Nina Bhat
(74) *Attorney, Agent, or Firm* — Birch, Stewart, Kolasch & Birch, LLP

(57) ABSTRACT

The present invention relates to a method for the deoxygenation of materials of biological origin and particularly to the removal of oxygen from biomass derived organic compounds with carbon monoxide, to yield linear and branched hydrocarbons suitable as biofuels or as blending stocks or components for biofuels, such as gas, gasoline, diesel fuel and aviation fuel, as well as solvents. The method comprises contacting a feedstock with carbon monoxide in the presence of a catalyst comprising a metal selected from a group consisting of ruthenium, manganese, rhodium, rhenium, osmium, iridium, molybdenum, copper, zinc, palladium, platinum and cobalt, in the presence of water, under alkaline conditions at a temperature from 150 to 350° C. and under a pressure from 0.1 to 150 bar, to produce hydrocarbons.

19 Claims, No Drawings

US 8,329,970 B2

DEOXYGENATION OF MATERIALS OF BIOLOGICAL ORIGIN

This Nonprovisional application claims priority under 35 U.S.C. §119(e) on U.S. Provisional Application No. 61/105,953 filed on Oct. 16, 2008.

FIELD OF THE INVENTION

The present invention relates to a method for the deoxygenation of materials of biological origin and particularly to the removal of oxygen from biomass derived organic compounds with carbon monoxide, to yield linear and branched hydrocarbons suitable as biofuels or as blending stocks or components for biofuels, such as gas, gasoline, diesel fuel and aviation fuel, as well as solvents. The present invention also relates to a method for the manufacture of paraffinic hydrocarbons from starting material of biological origin. The invention further provides an alternative method for the manufacture of high quality biofuels or blending stocks or components for biofuels based on biological starting materials.

BACKGROUND OF THE INVENTION

Environmental interests and an increasing demand for biofuels encourage fuel producers to employ more intensively renewable sources available for replacing petroleum-based feeds. In the manufacture of diesel fuels, the main interest has concentrated on vegetable oils and animal fats comprising triglycerides of fatty acids. Long, straight and mostly saturated hydrocarbon chains of fatty acids correspond chemically to the hydrocarbons present in diesel fuels. However, neat vegetable oils display inferior properties, particularly high viscosity and poor stability, and therefore their use in transportation fuels is limited.

Conventional approaches for converting vegetable oils or other natural materials containing fatty acids and fatty acid derivatives into liquid fuels comprise processes such as transesterification, catalytic hydrotreatment, hydrocracking, catalytic cracking without hydrogen and thermal cracking. Typically triglycerides, forming the main component in vegetable oils, are converted into the corresponding esters by the transesterification reaction with an alcohol in the presence of catalysts. The obtained product is fatty acid alkyl ester, most commonly fatty acid methyl ester (FAME). However, poor low-temperature properties of FAME, resulting from the straight chain nature of the molecule, limit its wider use in regions with colder climatic conditions. Thus double bonds are needed in order to create even bearable cold flow properties. Carbon-carbon double bonds and ester groups decrease the stability of fatty acid esters, which is a major disadvantage of transesterification technology. Further, it is also generally known that the presence of oxygen in esters results in undesired and higher emissions of $NO_x$ when compared to conventional diesel fuels.

Many biomass derived organic compounds could be suitable as fuels or their components, provided that their oxygen content is reduced. This is especially true with fatty acids derived both from animal and plant originating triglycerides. Oxygen can be removed by hydrodeoxygenation reactions, but the need of hydrogen is often excessive. The hydrodeoxygenation of oils and fats derived from biological material to hydrocarbons suitable as diesel fuel components is typically carried out in the presence of hydrogen and a catalyst under controlled hydroprocessing conditions.

During hydrodeoxygenation oxogroups are reacted with hydrogen and removed through formation of water. The hydrodeoxygenation reaction requires relatively high amounts of hydrogen. Due to the highly exothermic reactions the control of reaction heat is extremely important. Unnecessarily high reaction temperature, insufficient control of reaction temperature and unnecessarily low hydrogen availability in the feed stream cause formation of unwanted side reaction products and coking of catalyst. Side reactions, such as cracking, polymerisation, ketonisation, cyclisation and aromatisation decrease the yield and have negative impact on the properties of the product, such as the diesel fraction. Unsaturated feeds and free fatty acids in triglyceridic oils and fats derived from biological materials may also promote the formation of heavy molecular weight compounds. U.S. Pat. No. 5,705,722 describes a process for the production of diesel fuel additives by conversion of oils and fats derived from biological material into saturated hydrocarbons under hydroprocessing conditions. The process operates at high temperatures and produces n-paraffins and other hydrocarbons. The product has high cetane number but poor cold flow properties, which limit the amount of product that can be blended in conventional diesel fuel in the summer time and prevent its use during the winter time.

A two-step process is disclosed in patent FI 100248 for producing middle distillates from vegetable oils by hydrodeoxygenating fatty acids or triglycerides of vegetable oil origin using commercial sulphur removal catalysts to give n-paraffins, followed by isomerisation of said n-paraffins using metal containing molecule sieves or zeolites to obtain branched-chain paraffins. The hydrotreating is carried out at rather high reaction temperatures of 330-450° C. Hydrodeoxygenating fatty acids at those temperatures leads to shortened catalyst life resulting from coking and formation of side products.

EP 1 396 531 describes an alternative process containing at least two steps, the first one being a hydrodeoxygenation step and the second one being a hydroisomerisation step utilizing counter-current flow principle. Biological raw material containing fatty acids and/or fatty acid esters serves as the feedstock. The process may also comprise prehydrogenation and optional stripping steps.

Decarboxylation of carboxylic acids to hydrocarbons by contacting carboxylic acids with heterogeneous catalysts was suggested by Maier, W. F. et al.: Chemische Berichte (1982), 115(2), 808-12. Maier et al. tested $Ni/Al_2O_3$ and $Pd/SiO_2$ catalysts for decarboxylation of several carboxylic acids. During the reaction the vapors of the reactant were passed through a catalytic bed together with hydrogen. Hexane represented the main product of the decarboxylation of the tested compound heptanoic acid.

Biological raw materials often contain several impurities, such as metal compounds, organic nitrogen, sulphur or phosphorus containing compounds, said compounds being known catalyst inhibitors and catalyst poisons inevitably reducing the service life of catalysts and necessitating more frequent catalyst regeneration or replacing. Metals in oils and fats derived from biological material tend to build up on catalyst surfaces and they change the activity of the catalyst. Blocking of active sites of catalysts by metals typically decreases the activity of catalysts. Metals may promote some side reactions too.

Hydrolysis of triglycerides produces also diglycerides and monoglycerides, which are partially hydrolyzed products. Diglycerides and monoglycerides are surface-active compounds, which can form emulsions and make liquid/liquid separations of water and oil more difficult. Oils and fats derived from biological material may also contain other glyceride-like surface-active impurities like phospholipids containing phosphorus in their structures, such as lecithin. Phospholipids are gum like materials, which can be harmful to catalysts. Natural oils and fats also contain non-glyceride components. These are among others waxes, sterols, tocopherols and carotenoids, some metals and organic sulphur compounds as well as organic nitrogen compounds. These compounds can be harmful to catalysts or pose other problems in processing.

Oils and fats derived from biological material may contain free fatty acids, which are formed during processing of oils and fats through hydrolysis of triglycerides. Free fatty acids are a class of problematic components in bio oils and fats, their typical content being between 0 and 30% by weight. Free fatty acids are corrosive in their nature, they can attack the materials of process units and catalysts and, in the presence of metal impurities they can promote side reactions like formation of metal carboxylates. Due to the free fatty acids contained in oils and fats derived from biological material, the formation of heavy molecular weight compounds during processing is significantly increased when compared to triglyceridic feedstock having only low amounts of free fatty acids, typically below 1% by weight.

Fatty acid composition and the size and saturation degree of fatty acids may vary considerably in feeds of different origin. Melting point of oils and fats derived from biological material is mainly a consequence of saturation degree. Fats are more saturated than liquid oils and in this respect they need less hydrogen for the hydrogenation of double bonds. Double bonds in fatty acid chains contribute also to different kinds of side reactions, such as oligomerisation, polymerization, cyclisation, aromatisation and cracking reactions, which deactivate the catalyst, increase hydrogen consumption and reduce diesel yield.

Deoxygenation of plant oils and fats and animal oils and fats with hydrogen requires rather much hydrogen and at the same time releases significant amounts of heat. Heat is produced from deoxygenation reactions and from double bond hydrogenation. Different feedstocks produce significantly different amounts of reaction heat. The variation in reaction heat produced is mainly dependent of double bond hydrogenation. The average amount of double bonds in a triglyceride molecule can vary from about 1.5 to over 5 depending on the source of oil or fat.

Predominantly paraffinic or olefinic Fischer-Tropsch products obtained from synthesis gas derived from biomass contain also variable amounts of oxygenates, such as alcohols, ethers, carboxylic acids and esters of carboxylic acids. The amount and nature of said oxygenates depend on the carbon number range of the selected Fischer-Tropsch fraction and the Fischer-Tropsch process used in the processing. Particularly for fuel applications it is desirable to reduce the amounts of oxygenates.

Carbon monoxide has been used for the reduction of iron and other ores for a long time, and also in the field of organic chemistry reduction reactions with carbon monoxide are known.

In the reference: Thomson, W. J. and Laine, R. M., Homogeneous catalytic reduction of benzaldehyde with carbon monoxide and water. Applications of the water gas shift reaction. *ACS Symposium Series* (1981) 152 (Catal. Act. Carbon Monoxide), 133-45, the use of $Rh_6(CO)_{16}$, $Fe_3(CO)_{12}$ and $Ru_3(CO)_{12}$ as catalysts for studying the kinetics of benzaldehyde reductions with CO—$H_2O$ was disclosed.

According to literature, carbon monoxide reacts with alcohols, ethers and esters to give carboxylic acids. Suitable catalysts are rhodium and cobalt catalysts in the presence of iodine. This reaction is for example the basis for the commercial production of acetic acid, as presented in the following formula:

$$CH_3OH + CO \rightarrow CH_3COOH$$

Based on the above it can be seen that there exits an evident need for an alternative method for the deoxygenation of materials of biological origin and also for a method for decreasing the consumption of hydrogen when converting biomass derived feedstock to hydrocarbons, suitable as bio fuel.

OBJECT OF THE INVENTION

An object of the invention is a method for the deoxygenation of materials of biological origin using carbon monoxide.

A further object of the invention is a method for the removal of oxygen from materials of biological origin with carbon monoxide, to yield hydrocarbons suitable as biofuels or as blending stocks or components for biofuels or as solvents.

A further object of the invention is a method for the manufacture of paraffinic hydrocarbons from materials of biological origin.

A further object of the invention is an alternative method for the manufacture of high quality biofuels or blending stocks or components for biofuels, or solvents.

A further object of the invention is an alternative method for the manufacture of high quality diesel range hydrocarbons from oils and fats of biological origin with decreased hydrogen consumption and high diesel yield.

Characteristic features of the method according to the invention are provided in the claims.

DEFINITIONS

Biofuel means fuel derived from materials of biological origin, such as any biomass.

Here hydroprocessing is understood as catalytic processing of organic material by all means of molecular hydrogen.

Here hydrotreatment is understood as a catalytic process by all means of molecular hydrogen, which removes oxygen from organic oxygen compounds as water (hydrodeoxygenation, HDO), sulphur from organic sulphur compounds as dihydrogen sulphide ($H_2S$) (hydrodesulphurisation, HDS), nitrogen from organic nitrogen compounds as ammonia ($NH_3$) (hydrodenitrogenation, HDN) and halogens, such as chloride from organic chloride compounds as hydrochloric acid HCl (hydrodechlorination, HDCl), typically under the influence of a catalyst.

Here deoxygenation with carbon monoxide is understood to mean removal of oxygen with the aid of carbon monoxide (CO) from organic molecules, such as fatty acid derivatives, alcohols, ketones, aldehydes or ethers without added hydrogen.

Here hydrodeoxygenation of triglycerides or other fatty acid derivatives or fatty acids is understood to mean the removal of carboxyl oxygen as water by means of molecular hydrogen under the influence of a catalyst.

Here hydrocracking is understood as catalytic decomposition of organic hydrocarbon materials using molecular hydrogen at high pressures.

Here hydrogenation means saturation of carbon-carbon double bonds by means of molecular hydrogen under the influence of a catalyst.

Fischer-Tropsch process refers here to synthesis and processing for providing hydrocarbons from syngas or synthesis gas comprising a mixture of gas containing carbon monoxide and hydrogen generated by the gasification of carbon containing biological material.

Here n-paraffins mean normal alkanes or linear alkanes containing no side chains.

Here isoparaffins mean alkanes having one or more $C_1$-$C_9$ alkyl side chains, typically $C_1$-$C_2$ alkyl side chains, typically mono-, di-, tri- or tetramethylalkanes.

The feed (total feed) is to be understood comprising fresh feed and optionally at least one dilution agent.

Typical boiling range of gas is from −162° C. to 40° C. and typically gas comprises $C_1$-$C_5$ hydrocarbons.

Typical boiling range of gasoline is from 40° C. to 210° C. and typically gasoline comprises $C_5$-$C_{10}$ hydrocarbons.

Typically aviation fuel comprises $C_8$-$C_{16}$ hydrocarbons, and typically the initial boiling point is in the range 130° C. to 160° C. and final boiling point in the range 220° C. to 300° C.

Typical boiling range of diesel fuel is from 160° C. to 360° C. and typically diesel fuel comprises $C_{10}$-$C_{28}$ hydrocarbons.

Typically solvents comprise $C_6$-$C_{12}$ hydrocarbons.

Boiling temperatures refer to temperatures under normal atmospheric pressures unless otherwise provided.

SUMMARY OF THE INVENTION

The present invention is directed to a method for the deoxygenation of feedstock comprising materials of biological origin, the method comprising contacting the feedstock with carbon monoxide in the presence of a catalyst comprising a metal, in the presence of water under alkaline conditions at a temperature from 150° C. to 350° C. and under a pressure from 0.1 to 150 bar, to produce hydrocarbons. The resulting hydrocarbons are useful as high quality biofuels and as blending stocks or components for high quality fuels, as well as solvents. Particularly hydrocarbon components useful as diesel fuel are obtained as well as components suitable as gas, gasoline and aviation fuel and as blending stocks for said fuels.

Optionally the obtained hydrocarbons are isomerised at conditions sufficient to effect isomerisation or the obtained hydrocarbons are optionally hydrofinished at conditions sufficient to effect hydrofinishing.

DETAILED DESCRIPTION OF THE INVENTION

It was surprisingly found that carbon monoxide can be used for the deoxygenation of material of biological origin, such as biomass derived feedstock to yield hydrocarbons suitable as biofuels or as blending stocks or components for high quality fuels, or as solvents. Carbon monoxide acts as a reducing agent to remove oxygen from the molecules, resulting in the desired hydrocarbons, particularly paraffinic hydrocarbons.

The present invention is based on a simultaneous water-gas shift reaction (1) and deoxygenation reaction and it may also involve the Boudouart reaction (2). The reactions are described below:

$$CO + H_2O \rightarrow H_2 + CO_2 \quad (1)$$

$$2CO \leftrightarrow C + CO_2 \quad (2)$$

Possible reactions relating to the reduction with carbon monoxide are presented below using rapeseed oil methyl ester as an example. Rapeseed oil methyl ester is allowed to react with carbon monoxide whereby oxygen is subtracted from the carbonyl group (3), followed by removal of the oxygen from the ether bond (4):

$$R-CH_2-CH_2-COOCH_3 + CO \rightarrow R-CH_2-CH=CHOCH_3 + CO_2 \quad (3)$$

$$R-CH_2-CH=CHOCH_3 + CO \rightarrow R-CH_2-CH=CHCH_3 + CO_2 \quad (4)$$

Thermodynamic calculations based on reactions (3) and (4) also confirmed that when these reactions are carried out simultaneously the equilibrium is on the product side already at moderate temperatures under atmospheric pressure.

The present invention provides means for using carbon monoxide as a reducing agent in upgrading material of biological origin and particularly biomass derived feedstock to biofuels or to components of fuels or to solvents. Suitably the feedstock is selected from carboxylic acids, esters of carboxylic acids, alcohols, aldehydes and ethers, having carbon number between C3 and C70, Fischer-Tropsch products and fractions, and any mixtures thereof, preferably $C_3$-$C_{40}$ carboxylic acids, esters of $C_3$-$C_{40}$ carboxylic acids, $C_3$-$C_{40}$ alcohols, $C_3$-$C_{40}$ aldehydes and $C_3$-$C_{40}$ ethers.

Carbon monoxide is a fairly strong reducing agent with several industrial applications in the chemical industry. At oil refineries it is available for example from steam reforming processes, where methane and water are used for producing hydrogen and CO, which is typically further reacted to $CO_2$. Carbon monoxide can also be conveniently obtained for example as a side-product from processes utilizing biomass waste material, from partial oxidation of hydrocarbons and from hydrogen manufacturing processes.

The method according to the present invention for the deoxygenation of feedstock comprising materials of biological origin comprises the steps where the feedstock is contacted with carbon monoxide in the presence of a catalyst comprising a metal, in the presence of water under alkaline conditions at a temperature from 150 to 350° C. and under a pressure from 0.1 to 150 bar, to produce hydrocarbons. The biomass-derived feedstock is allowed to react with carbon monoxide under conditions sufficient to effect the deoxygenation to yield hydrocarbons, particularly paraffinic hydrocarbons.

Optionally the hydrocarbons are isomerised or optionally the hydrocarbons are subjected to hydrofinishing.

The resulting hydrocarbons are separated to fractions or components useful as high quality biofuels and as blending stocks or components for high quality fuels, or as solvents, particularly as diesel fuel, gas, gasoline and aviation fuel.

Feedstock

Materials of biological origin (biomass derived materials), such as carboxylic acids, esters of carboxylic acids, alcohols, aldehydes and ethers, having carbon number between C3 and C70, Fischer-Tropsch products and fractions, and any mixtures thereof, preferably $C_3$-$C_{40}$ carboxylic acids, esters of $C_3$-$C_{40}$ carboxylic acids, $C_3$-$C_{40}$ alcohols, $C_3$-$C_{40}$ aldehydes and $C_3$-$C_{40}$ ethers are suitably used as the feedstock in the method according to the invention.

The feedstock may comprise Fischer-Tropsch products or fractions obtained from processing of biomass derived starting materials. Said products or fractions comprise oxygenates in addition to paraffinic and/or olefinic compounds.

The feedstock may comprise oils and/or fats originating from biological and renewable sources, for example fats and oils originating from plants and/or animals and/or fish and/or insects and compounds derived from them as well as oils and fats and oils obtained from microbiological processes. Said oils and fats typically comprise $C_{12}$-$C_{24}$ fatty acids, derivatives thereof, such as esters of fatty acids as well as triglycerides of fatty acids or combinations of thereof. Fatty acids or fatty acid derivatives, such as esters may be produced via hydrolysis of said oils and fats or by their fractionalization or transesterification reactions of triglycerides or by microbiological processes utilizing algae or microbes, such as yeasts, molds or bacteria.

The basic structural unit of said oil or fat is a triglyceride, but typically also diglycerides and free fatty acids are comprised therein. Triglyceride is a triester of glycerol with three fatty acid molecules, having the structure presented in the following formula I:

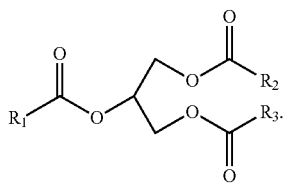

Formula 1

Structure of triglyceride

In formula I $R_1$, $R_2$ and $R_3$ are alkyl chains. Fatty acids found in natural triglycerides are almost solely fatty acids of even carbon number. Therefore $R_1$, $R_2$, and $R_3$ typically are $C_5$-$C_{23}$ alkyl groups, mainly $C_{11}$-$C_{19}$ alkyl groups and most typically $C_{15}$ or $C_{17}$ alkyl groups. $R_1$, $R_2$, and $R_3$ may contain carbon-carbon double bonds. These alkyl chains can be saturated, unsaturated or polyunsaturated.

Suitable oils and fats are plant and vegetable oils and fats, animal oils and fats, fish oils, and fats and oils obtained from by microbiological processes utilizing algae or microbes, such as yeasts, molds or bacteria, and mixtures thereof. Examples of wood-based and other plant-based fats and oils are rapeseed oil, colza oil, canola oil, tall oil, sunflower oil, Jatropha seed oil, soybean oil, hempseed oil, olive oil, linseed oil, mustard oil, palm oil, peanut oil, castor oil, coconut oil, as well as fats contained in plants bred by means of gene manipulation. Examples of animal oils and fats are lard, tallow, train oil, and fats contained in milk. Additionally algae oil as well as recycled fats of the food industry and mixtures of the above can be mentioned.

In many cases the oil feed, such as crude plant oil or crude animal fat is not suitable as such in the processing because of high impurity content. Thus the feed is preferably pretreated using suitably one or more conventional purification procedures before introducing it to the deoxygenation step. Examples of some conventional procedures are provided below.

Degumming of plant oils/fats and animal oils/fats refers to the means for the removal of phosphorus compounds, such as phospholipids. Solvent extracted vegetable oils often contain significant amounts of gums, which are mostly phospholipids.

Degumming is typically performed by washing the feed at elevated temperatures and pressures with an acid, base and soft water, followed by separation of the gums formed. A major amount of metal components, typically in the form of metal-phosphatide complexes, are also removed from the feedstock during the degumming procedure.

A feed, which is optionally degummed or refined in any other conventional way, may be bleached. In the bleaching the feed is heated and mixed with natural or acid-activated bleaching clay. Bleaching removes various impurity traces left from other pretreatment steps, such as chlorophyll, carotenoids, phospholipids, metals, soaps and oxidation products.

Optionally the double bonds of the triglyceride structures of the feed may be prehydrogenated at reduced hydrogenation reaction temperature with NiMo or other suitable catalyst, prior to the deoxygenation in order to prevent double bond polymerisation of unsaturated triglycerides.

In the following the deoxygenation step and the optional isomerisation and hydrofinishing steps are described in more detail.

Deoxygenation

In the deoxygenation step the biomass derived components of the feedstock, such as fatty acids, triglycerides and other fatty acid derivatives as well as Fischer-Tropsch products or fractions are deoxygenated with carbon monoxide in the presence of a metal catalyst and water under alkaline conditions to yield hydrocarbons, particularly paraffinic hydrocarbons.

The deoxygenation conditions include a temperature from 150 to 350° C. and a pressure from 0.1 to 150 bar. Preferably the temperature is from 200 to 300° C. The pressure is preferably from 1 to 100 bar. In the case the catalyst comprises a metal carbonyl complex the pressure ranges preferably from 2 to 100 bar. When the metal carbonyl complex is formed in-situ the pressure ranges preferably from 30 to 100 bar.

The molar amount of water used is ±25 mol % with respect to the molar amount of carbon monoxide used. Carbon monoxide is used in an amount corresponding to at least the stoichiometric amount calculated from the oxygen content of the feedstock.

The deoxygenation step is carried out under alkaline conditions and particularly at a pH of 7 or more than 7 (7-14). The pH of the reaction mixture is adjusted to the desired range with alkali metal hydroxide or alkaline earth metal hydroxide or an aqueous solution containing it. Suitably NaOH is used.

Advantageously the reaction conditions in the deoxygenation step are selected to be suitable for maintaining the feedstock and the products in liquid phase.

Typical reaction time is typically between 1 and 30 hours.

Suitably fixed-bed reactors and continuous mixing tank reactors may for example be used.

Deoxygenation of the biomass-derived compounds, such as triglycerides facilitates controlled decomposition of the triglyceride molecule. Light hydrocarbons and gases formed, such as methane, ethane, propane, butane and water and $CO_2$ are separated from the deoxygenated product together with any unreacted carbon monoxide.

Deoxygenation Catalyst

Suitable deoxygenation catalysts are selected from homogeneous and heterogeneous catalysts comprising a metal selected from the group consisting of iron, ruthenium, manganese, rhodium, rhenium, osmium, iridium, molybdenum, copper, zinc, palladium, platinum and cobalt, preferably the metal is cobalt, molybdenum, ruthenium or manganese. The metal in the catalyst is in the form of a carbonyl complex or as elemental metal or as oxide or a nitrate salt or halogen salt and preferably a metal carbonyl complex is used. An example of a suitable metal carbonyl complex is $Ru_3(CO)_{12}$. The metal carbonyl complex may also be manufactured in situ in the reactor.

Preferably the deoxygenation catalyst is supported on a carrier selected from carbon, alumina, silica, mesoporous silica alumina, clays, calcium carbonate, aluminium hydrocalcite and magnesium hydrocalcite. Particularly preferably a catalyst comprising a metal carbonyl complex on silica or alumina or mesoporous silica alumina carrier, or an elemental metal on carbon catalyst, which forms the carbonyl complex in situ, are used.

The metal carbonyl complex may be prepared in situ in the reactor from the elemental metal, metal salt or metal oxide and carbon monoxide prior to introducing the reactants. The metal carbonyl complex may also be formed during the start up of the reaction.

The metal carbonyl complexes may be prepared in several alternative ways known in the art and they are also commercially available. Synthetic routes include direct reaction of carbon monoxide with elemental metal or metal salt or metal complex, reductive carbonylation, photolysis and thermolysis reactions. For example dicobalt octacarbonyl ($Co_2(CO)_8$) is obtainable from the reaction of cobalt acetate with carbon monoxide, and dimanganese decacarbonyl ($Mn_2(CO)_{10}$) from manganese acetate with carbon monoxide, using triethylaluminium as reducing agent. Molybdenum hexacarbonyl ($Mo(CO)_6$), triiron dodecacarbonyl ($Fe_3(CO)_{12}$) and triruthenium dodecacarbonyl ($Ru_3(CO)_{12}$) are obtainable from the corresponding metal chlorides with carbon monoxide under pressure.

The amount of the metal catalyst used is from 0.1 to 20 wt % calculated from amount of the feed.

Optional Isomerisation

The deoxygenation step may optionally be followed by an isomerisation step where the hydrocarbons, such as n-paraffins obtained in the deoxygenation step are converted to isomerised products, such as isoparaffins. Simultaneously possibly remaining double bonds are hydrogenated when hydrogen is used in the isomerisation.

In the optional isomerisation step the product or a fraction obtained from the deoxygenation step is isomerised, optionally in the presence of hydrogen, in the presence of an isomerisation catalyst under the reaction conditions including a pressure between 20 and 150 bar, preferably between 30 and 100 bar and a temperature between 200 and 500° C., preferably between 280 and 400° C.

The isomerisation catalyst comprises a hydrogenation component and an acidic support with carrier. The hydrogenation component is a metal selected from Group VIII of the Periodic Table of Elements, preferably nickel, platinum or palladium. The acidic support is suitably alumina, zirconium oxide or a molecular sieve selected from zeolites and silicoaluminophosphates. Alumina, chlorine activated alumina, silica and zirconium oxide are suitable carriers. Preferably the isomerization catalyst contains SAPO-5, SAPO-11 or SAPO-41 or ZSM-22 or ZSM-23, mordenite or ferrierite Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. Suitable isomerisation catalysts for paraffins in the gasoline pool are Pt/mordenite/$Al_2O_3$, Pt/Cl-activated $Al_2O_3$, and for paraffins in the middle distillate range Pt/ZSM-22/$Al_2O_3$, Pt/ZSM-23/$Al_2O_3$, Pt/SAPO-11/$SiO_2$, Pt/SAPO-11/$Al_2O_3$. Most of these catalysts require the presence of hydrogen to reduce the catalyst deactivation.

The isomerisation step yields products with more branching, thus having improved properties, such as improved cold flow properties, freezing point, cetane number and octane number, particularly relevant for aviation fuel, gasoline and diesel fuel of EN590 quality.

Optional Hydrofinishing

When only paraffinic hydrocarbons are desired, optional hydrofinishing of the product obtained from the deoxygenation step may be needed for the hydrogenation of remaining double bonds. The hydrofinishing can be performed with any conventional hydrogenation methods. The hydrogenation catalysts used for the hydrofinishing typically contain metal (s) selected from nickel, palladium, platinum, rhodium, cobalt, molybdenum, or their alloys or mixtures, and a carrier selected from alumina, silica, silica alumina, clay or zeolite. The metals can be in reduced or in sulphidised form in the catalyst. The hydrofinishing temperatures are in the range of 50-400° C., preferably in the range of 80-360° C., and pressures are in the range of 10-150 bar.

It was surprisingly found that carbon monoxide may effectively be used for the deoxygenation of biomass derived organic compounds containing oxygen, thus replacing the use of hydrogen. The reaction is carried out at relatively low reaction temperatures, where particularly catalysts based on metal carbonyl complexes are suitable. Said catalysts are able to activate the carbon-oxygen bond, thus facilitating the removal of oxygen.

Significantly lower reaction temperatures are used in the deoxygenation step carried out according to the present invention than in conventional hydrodeoxygenation methods, resulting is less undesired cracking. Thus also free fatty acids in the feedstock can be used effectively in the method.

The method according to the present invention offers possibilities to use the carbon monoxide streams generally available at oil refineries. It also results in significant savings in hydrogen consumption, as well as savings in investments and operations.

Additionally, because no added hydrogen is needed in the deoxygenation step the $CO_2$ emissions are avoided because hydrogen is typically produced from natural gas in a conventional manner resulting in significant $CO_2$ emissions.

The resulting liquid hydrocarbons, typically paraffinic hydrocarbons, are useful as high quality biofuels and as blending stocks or components for high quality fuels, particularly as diesel fuel, gas, gasoline and aviation fuels, and also as solvents.

The process also yields isoparaffinic hydrocarbons particularly suitable as high quality fuels and components for biofuels in an efficient and economic way from biological and renewable material and from any mixtures thereof.

The invention is further illustrated with the following examples, which however are not intended to limit the scope the invention.

EXAMPLES

In the examples the liquid/solid products were analysed by gas chromatography and mass spectrometry. The sample was dissolved in hot toluene (CHROMASOLV Plus for HPLC, >99.9%, Sigma-Aldrich), filtered and injected to the gas chromatograph. The column of gas chromatography was DB-WAX 30 m, I.D:0.25 mm, film: 0.5 μm.

The values in volume % given in the examples are calculated from the GC-analysis using calibrated response factors.

The conversion was calculated for simplification from the sum of stearic acid and methyl stearate. Conversion values means: 100-area percent of stearic acid (GC)-area percent of methyl stearate (GC).

Example 1

Deoxygenation of Stearic Acid

Deoxygenation of stearic acid (purity 95%) (reactant) was performed in a Parr reactor with ruthenium carbonyl catalyst. Before the reaction, the reactor was loaded with 5.3 g of $Ru_3(CO)_{12}$ catalyst, 24 g of stearic acid, and 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 70 bar at reaction temperature of 250° C., the reaction time being 24 h. The conversion was 72%. The results are presented in the following as % by volume:

| | |
|---|---|
| n-C17 paraffins | 53.6% |
| Total paraffins | 61.6% |
| Total hydrocarbons | 69.9% |
| Total esters | 2.5% |
| Stearic acid | 27.7% |

Example 2

Deoxygenation of Palm Oil

Deoxygenation of 5 g of palm oil (reactant) was performed in a Parr reactor with 5.3 g of $Ru_3(CO)_{12}$ catalyst. Before the reaction, the reactor was loaded with the catalyst, reactant, 4.5 g of water and 0.33 g of sodium hydroxide. After the loading of the reactant, the reactor was pressurized to 80 bar of nitrogen for studying the tightness of the system. Then the reactor was depressurised and filled with carbon monoxide to a desired pressure initially of 30 bar, rising to 70 bar at reaction temperature of 250° C., the reaction time being 24 h. The results are presented in the following as % by volume:

| | |
|---|---|
| n-C15 paraffins | 8.5% |
| n-C17 paraffins | 16.9% |
| Total paraffins | 50.0% |
| Total hydrocarbons | 52.3% |
| Total esters | 1.2% |
| Palmitic acid | 19.0% |
| Stearic acid | 18.6% |

Example 3

Deoxygenation of Stearic Acid

Deoxygenation of stearic acid (purity 95%) (reactant) was performed in a Parr reactor with ruthenium carbonyl catalyst. Before the reaction, the reactor was loaded with 5.3 g of $Ru_3(CO)_{12}$ catalyst, 4.8 g of stearic acid, 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 68 bar at reaction temperature of 250° C., the reaction time being 24 h. The results are presented in the following as % by volume:

| | |
|---|---|
| n-C17 paraffins | 41.3% |
| Total paraffins | 70.5% |
| Total hydrocarbons | 71.7% |
| Total esters | 11.7% |
| Stearic acid | 0.3% |

Example 4

Deoxygenation of Methyl Stearate

Deoxygenation of methyl stearate (purity 97%) (reactant) was performed in a Parr reactor with ruthenium carbonyl catalyst. Before the reaction, the reactor was loaded with 5.3 g of $Ru_3(CO)_{12}$ catalyst, 5.0 g of methyl stearate, 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 83 bar at reaction temperature of 250° C., the reaction time being 24 h. The results are presented in the following as % by volume:

| | |
|---|---|
| n-C17 paraffins | 27.0% |
| Total paraffins | 49.2% |
| Total hydrocarbons | 50.3% |
| Methyl stearate | 34.0% |

Example 5

Deoxygenation of Methyl Stearate

Deoxygenation of methyl stearate (purity 97%) (reactant) was performed in a Parr reactor with ruthenium carbonyl catalyst. Before the reaction, the reactor was loaded with 5.3 g of $Ru_3(CO)_{12}$ catalyst, 25.0 g of methyl stearate, 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 83 bar at reaction temperature of 250° C., the reaction time being 24 h. The results are presented in the following as % by volume:

| | |
|---|---|
| n-C17 paraffins | 28.4% |
| Total paraffins | 35.2% |
| Total hydrocarbons | 35.8% |
| Methyl stearate | 1.4% |
| Stearic acid | 58.3% |

Example 6

Deoxygenation of Methyl Stearate

Deoxygenation of methyl stearate (purity 97%) (reactant) was performed in a Parr reactor with ruthenium catalyst. Before the reaction, the reactor was loaded with 5.3 g of Ru on carbon, 25.0 g of methyl stearate, 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 74 bar at reaction temperature of 250° C., the reaction time being 24 h. The conversion was 73.1%. The results are presented in the following as % by volume:

| | |
|---|---|
| n-C17 paraffins | 26.4% |
| n-C18 paraffins | 2.1% |
| Methyl stearate | 18.8% |

Example 7

Deoxygenation of Methyl Stearate

Deoxygenation of methyl stearate (purity 97%) (reactant) was performed in a Parr reactor with ruthenium carbonyl catalyst. Before the reaction, the reactor was loaded with 5.3 g of $Ru_3(CO)_{12}$ on silica carrier ($SiO_2$), 12.5 g of methyl stearate, 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 83 bar at reaction temperature of 250° C., the reaction time being 24 h. The conversion was 72%. The results are presented in the following as % by volume:

| | |
|---|---|
| n-C17 paraffins | 21.6% |
| n-C18 paraffins | 2.3% |
| Methyl stearate | 24.7% |

Example 8

Deoxygenation of Stearic Acid

Deoxygenation of stearic acid (purity 95%) (reactant) was performed in a Parr reactor with manganese carbonyl catalyst. Before the reaction, the reactor was loaded with 5.75 g of $Mn_2(CO)_{10}$ catalyst, 12 g of stearic acid, and 4.5 g of water and 0.33 g of sodium hydroxide, the molar ratio of water to NaOH being 30. After the loading of the reactant, the reactor was pressurized to 80 bar of nitrogen for studying the tightness of the system. Then the reactor was depressurised and filled with carbon monoxide to an initial pressure of 30 bar, rising to 70 bar at reaction temperature of 230° C., the reaction time being 5 h. The results are presented in the following as % by volume:

| | |
|---|---|
| n-C17 paraffins | 23.4% |
| Total paraffins | 26.3% |
| Stearic acid | 12.0% |

Example 9

Deoxygenation of Methyl Stearate

Deoxygenation of methyl stearate (purity 97%) (reactant) was performed in a Parr reactor with ruthenium carbonyl catalyst. Before the reaction, the reactor was loaded with 5.3 g of $Ru_3(CO)_{12}$ catalyst, 25 g of methyl stearate, 4.5 g of water and 0.33 g of sodium hydroxide, the molar ratio of water to NaOH being 30. After the loading of the reactant, the reactor was pressurized to 80 bar of nitrogen. Then the reactor was depressurised and filled with carbon monoxide to an initial pressure of 30 bar, rising to 70 bar at reaction temperature of 300° C., the reaction time being 24 h. The results are presented in the following as % by volume:

| | |
|---|---|
| n-C17 paraffins | 17.3% |
| n-C18 paraffins | 0.8% |
| Total paraffins | 21.8% |
| Olefins | 12.9% |
| Total hydrocarbons | 37.2% |
| Methyl stearate | 17.9% |

Example 10

Comparison of Activities of Catalysts

Comparison of activities of different metal carbonyl catalysts was carried out in the reaction when using stearic acid as the reactant. The reaction was performed in a Parr reactor. Before the reaction, the reactor was loaded with the catalyst, stearic acid water and sodium hydroxide. After the loading of the reactant, the reactor was pressurized to 80 bar of nitrogen. Then the reactor was depressurised and filled with carbon monoxide to an initial pressure of 40 bar, rising to 70 bar, the reaction time being 5 h in each case. The results are presented in the following table 1.

TABLE 1

| | Metal carbonyl | | | | | | | |
|---|---|---|---|---|---|---|---|---|
| | Ru | Mo | Mo | Fe | Fe | Co | Co | Mn |
| Reaction T (° C.) | 230 | 230 | 250 | 230 | 250 | 230 | 250 | 230 |
| Stearic acid (area-%) | 30 | 84 | 19 | 50 | 55 | 6 | 35 | 2 |
| Conversion (%) | 70 | 16 | 81 | 50 | 65 | 94 | 45 | 98 |

The invention claimed is:

1. A method for the deoxygenation of feedstock comprising materials of biological origin, the method comprising contacting the feedstock with carbon monoxide in the presence of a catalyst comprising a metal selected from a group consisting of ruthenium, manganese, rhodium, rhenium, osmium, iridium, molybdenum, copper, zinc, palladium, platinum and cobalt, in the presence of water, under alkaline conditions at a temperature from 150 to 350° C. and under a pressure from 0.1 to 150 bar, to produce hydrocarbons.

2. The method according to claim 1, wherein the temperature is from 200 to 300° C. and the pressure is from 1 to 100 bar.

3. The method according to claim 1, wherein the metal is present as an elemental metal or a metal carbonyl complex or a halogen salt of a metal or a nitrate salt of a metal.

4. The method according to claim 3, wherein the metal comprises a metal carbonyl complex manufactured in situ from carbon monoxide and the elemental metal or a salt of the metal or an oxide of the metal.

5. The method according to claim 1, wherein the metal is cobalt or molybdenum or ruthenium or manganese.

6. The method according to claim 1, wherein the catalyst is supported on carrier selected from carbon, alumina, silica, mesoporous silica alumina, clays, calcium carbonate, aluminum hydrocalcite and magnesium hydrocalcite.

7. The method according to claim 1, wherein the catalyst is a metal carbonyl catalyst comprising cobalt or molybdenum or ruthenium or manganese.

8. The method according to claim 1, wherein the feedstock is selected from the group consisting of fats and oils originating from plants or animals or fish or insects, fats and oils obtained from microbiological processes utilizing algae or microbes, fats and oils contained in plants bred by means of gene manipulation, recycled fats of the food industry, biomass originating Fischer-Tropsch products and fractions, and mixtures thereof.

9. The method according to claim 1, wherein the feedstock is selected from the group consisting of carboxylic acids, esters of carboxylic acids, alcohols, aldehydes and ethers having carbon number between C3 and C70, and mixtures thereof.

10. The method according to claim 9, wherein the feedstock is selected from the group consisting of $C_3$-$C_{40}$ carboxylic acids, esters of $C_3$-$C_{40}$ carboxylic acids, $C_3$-$C_{40}$ alcohols, $C_3$-$C_{40}$ aldehydes, $C_3$-$C_{40}$ ethers, and mixtures thereof.

11. The method according to claim 1, further comprising isomerisation of the product or of a fraction obtained from the deoxygenation.

12. The method according to claim 11, wherein the isomerisation conditions include a pressure between 20 and 150 bar and a temperature between 200 and 500° C. and the isomerisation catalyst comprises a hydrogenation component and an acidic support with carrier.

13. The method according to claim 11, further comprising hydrofinishing of the product or of a fraction obtained from the deoxygenation.

14. The method according to claim 12, further comprising hydrofinishing of the product or of a fraction obtained from the deoxygenation.

15. The method according to claim 14, wherein the hydrofinishing conditions include a temperature between 50 and 400° C. and a pressure between 10 and 150 bar and the hydrofinishing catalyst comprises a metal on a carrier.

16. The method according to claim 1 further comprising hydrofinishing of the product or a fraction obtained from the deoxygenation.

17. The method according to claim 16, wherein the hydrofinishing conditions include a temperature between 50 and 400° C. and a pressure between 10 and 150 bar and the hydrofinishing catalyst comprises a metal on a carrier.

18. The method according to claim 1, wherein hydrocarbons useful as diesel fuel, gas, gasoline and aviation fuel and as solvents are obtained.

19. The method according to claim 1, wherein paraffinic hydrocarbons are obtained.

* * * * *